United States Patent
Pesch

(10) Patent No.: US 8,557,023 B2
(45) Date of Patent: Oct. 15, 2013

(54) DEVICE FOR PREPARING A GAS FLOW FOR INTRODUCTION THEREOF INTO A MASS SPECTROMETER

(75) Inventor: Reinhold Pesch, Weyhe (DE)

(73) Assignee: Thermo Fisher Scientific (Bremen) GmbH, Bremen (DE)

(*) Notice: Subject to any disclaimer, the term of this patent is extended or adjusted under 35 U.S.C. 154(b) by 251 days.

(21) Appl. No.: 12/935,260

(22) PCT Filed: Mar. 18, 2009

(86) PCT No.: PCT/EP2009/001983
§ 371 (c)(1),
(2), (4) Date: Oct. 20, 2010

(87) PCT Pub. No.: WO2009/118122
PCT Pub. Date: Oct. 1, 2009

(65) Prior Publication Data
US 2011/0036238 A1      Feb. 17, 2011

(30) Foreign Application Priority Data
Mar. 28, 2008   (DE) .......................... 10 2008 016 342

(51) Int. Cl.
*B01D 53/22*   (2006.01)
(52) U.S. Cl.
USPC .................... 95/53; 95/45; 96/4; 96/8; 96/10; 96/413; 73/863.23

(58) Field of Classification Search
USPC .......... 95/45, 53; 96/4, 8, 10, 413; 73/863.21, 73/863.23
See application file for complete search history.

(56) References Cited

U.S. PATENT DOCUMENTS

| | | | | |
|---|---|---|---|---|
| 3,430,417 A * | 3/1969 | Cree | ................................. | 95/53 |
| 3,455,092 A * | 7/1969 | Llewellyn | .......................... | 96/5 |
| 3,662,520 A * | 5/1972 | Saunders | .......................... | 96/10 |
| 4,482,360 A * | 11/1984 | Taketomo et al. | ................ | 95/53 |
| 5,012,052 A * | 4/1991 | Hayes | .......................... | 73/23.37 |
| 5,013,437 A * | 5/1991 | Trimmer et al. | .................. | 95/53 |
| 2005/0223779 A1 | 10/2005 | Perkins et al. | | |

FOREIGN PATENT DOCUMENTS

WO   WO 89/09486 A1   10/1989

* cited by examiner

*Primary Examiner* — Jason M Greene
(74) *Attorney, Agent, or Firm* — Charles B. Katz; Nicholas Cairns

(57) ABSTRACT

The invention relates to a device for preparing a gas flow for introduction thereof into a mass spectrometer, wherein the gas flow contains one or more analytes and has helium as carrier gas. According to the invention, a selective separating device is provided for separating off a part of the carrier gas from the gas flow (10), to form a residual gas flow (11) and a separated carrier gas flow (12). A higher fraction of the analyte is present therein than in the gas flow and in the separated carrier gas flow there is a lower fraction of the analyte.

9 Claims, 4 Drawing Sheets

DEVICE FOR PREPARING A GAS FLOW FOR INTRODUCTION THEREOF INTO A MASS SPECTROMETER

BACKGROUND OF THE INVENTION

The invention relates to a device for preparing a gas stream before feed of same to a mass spectrometer, in particular for determining isotope ratios, wherein the gas stream contains carrier gas and one or more analytes.

Mass spectrometers for determining the isotope ratios of gases analyze only pure simple gases, such as $CO_2$ and $N_2$. Most of the substances that are to be analyzed are not present as pure gases. Therefore the substances must be converted into pure simple gases. This conversion process is preferably carried out in a carrier gas stream. As carrier gas, in particular helium is used. This is an on-line method.

Only a limited amount of carrier gas or helium can be fed to the ion source of the mass spectrometer. Typically, the appliances for preparing the gases that are arranged upstream of the mass spectrometer operate with a higher carrier gas stream or helium stream than can be fed to the mass spectrometer. This applies in particular to element analyzers.

For solving this problem, the gas stream containing the carrier gas or helium on the one hand and the pure simple gas—the analyte—on the other can be divided, such that only a relatively small carrier gas stream or helium stream passes into the mass spectrometer, while the remaining part of the gas stream is disposed of. It is a disadvantage in this case that a relatively large subquantity of the analyte is also disposed of and does not pass into the mass spectrometer.

U.S. Pat. No. 5,012,052 discloses a method for isotope ratio determination. A sample passes with a hydrogen carrier gas into a gas chromatograph. Subsequent to the latter, a selectively active membrane having a palladium coating is provided at which the hydrogen carrier gas is separated. At the same time the hydrogen carrier gas is replaced by helium as carrier gas.

The purpose of the present invention is providing a larger subquantity of the analyte than previously.

SUMMARY OF THE INVENTION

The device according to the invention is characterized by a selectively acting separating appliance for separating off some of the helium carrier gas from the gas stream and for forming a residual gas stream and a carrier gas stream separated off therefrom, wherein in the residual gas stream there is a higher proportion of the analyte than in the gas stream and wherein in the separated carrier gas stream there is a lower proportion of the analyte than in the gas stream. By means of the device according to the invention, the residual gas stream is enriched with the analyte. What is sought is a development of the device according to the invention in such a manner that the carrier gas in the separated carrier gas stream as far as possible no longer contains analyte. The analyte is then contained completely in the residual gas stream. However, any solution is advantageous in which the proportion of the analyte in the residual gas stream is merely higher than in the gas stream. The basic concept of the invention is that some of the carrier gas and as small an amount as possible of the analyte are separated off from the gas stream.

The carrier gas used is preferably helium. The invention is particularly advantageous combined with a combination of gas chromatograph and isotope mass spectrometer (GC-IRMS) or element analyzer and isotope mass spectrometer (EA-IRMS). The use of the invention, precisely in this combination, leads to an improvement of the sensitivity of the overall system.

According to the invention it is provided that the separating appliance does not change the isotope ratios of the analyte or analytes. The properties of the selectively acting separating appliances must be matched and selected in accordance with this requirement. No isotope fractionation must occur. The isotope ratio of the analyte in the gas stream must correspond to the isotope ratio of the analyte in the residual gas stream.

According to a further concept of the invention, the separating appliance has a membrane for separating off the carrier gas stream. The membrane should preferably be permeable to the carrier gas or helium. Some of the carrier gas passes from a front side of the membrane to a rear side of same, whereas the analyte, because of the selective property of the membrane, remains completely or for the most part on the front side of the membrane.

The expression "membrane" is first of all to be understood functionally. In the broadest sense it is a layer permeable to the carrier gas, wherein this layer need not be constructed to be flat or planar, but can also form the wall of a tube or capillary. The "front side" of the membrane is then the interior of the capillary, while the "rear side" is the volume surrounding the capillary.

According to a further concept of the invention, the membrane consists of silicon dioxide ($SiO_2$ or quartz) or of a polymer material. A heating appliance for heating the membrane can be assigned to the membrane. Silicon dioxide especially has particularly good separation properties with respect to the permeability of helium at temperatures of 300° C. to 900° C., or from 600° C. to 700° C.

According to a further concept of the invention, a volume conducting the separated carrier gas stream is provided, which volume has a reduced pressure compared with a volume conducting the gas stream. The carrier gas is separated off from the gas stream in the separating appliance, supported by the pressure difference between the two said volumes.

Advantageously, a pump appliance is provided for pumping off the separated carrier gas stream. By means of the pump appliance, the abovementioned pressure difference can also be generated.

According to a further concept of the invention, a purging appliance is provided for purging the volume conducting the separated carrier gas stream. A gas source with a gas reservoir can be assigned to the purging appliance. A purging gas flows from the gas reservoir into said volume and purges any carrier gas still containing the analyte. As purging gas, in particular a gas different from the carrier gas is provided, e.g. nitrogen ($N_2$).

Advantageously, one or more capillaries are provided in the separating appliance. These capillaries have walls that are permeable to the carrier gas (membrane walls). The type and number of the capillaries are also dependent on the materials and premises available. A single capillary in the form of a more or less densely packed spiral is possible. Alternatively, a plurality of capillaries can be provided in parallel to one another and be more or less tightly packed or coiled.

The walls of the capillaries are preferably permeable to the carrier gas or helium, but not to the analyte.

According to a further concept of the invention, a volume is attached to the outside of the capillaries, which volume has a reduced pressure compared with the interior of the capillaries. A pump appliance can be attached to said volume for generating the reduced pressure. The pressure difference improves the separation properties of the capillaries.

Corresponding to a further concept of the invention, a purging appliance is provided for purging a volume attached to the outside of the capillaries. Preferably, the purging gas used is a gas different from the carrier gas, e.g. nitrogen from a corresponding gas reservoir.

The invention also relates to a mass spectrometer, in particular for determining isotope ratios, with a device according to the invention corresponding to the above details.

The invention also relates to a system containing a gas chromatography appliance, a mass spectrometer, in particular isotope mass spectrometer, and a device according to the invention corresponding to the details above. Alternatively to, or in addition to, the gas chromatography appliance, an element analyzer can also be provided.

Finally, the invention also relates to a method for preparing a gas stream.

BRIEF DESCRIPTION OF THE DRAWINGS

Further features of the invention result from the description in passing and from the claims. Advantageous exemplary embodiments of the invention will be described in more detail hereinafter with reference to drawings. In the drawings:

DETAILED DESCRIPTION OF EMBODIMENTS OF INVENTION

Figure 1:
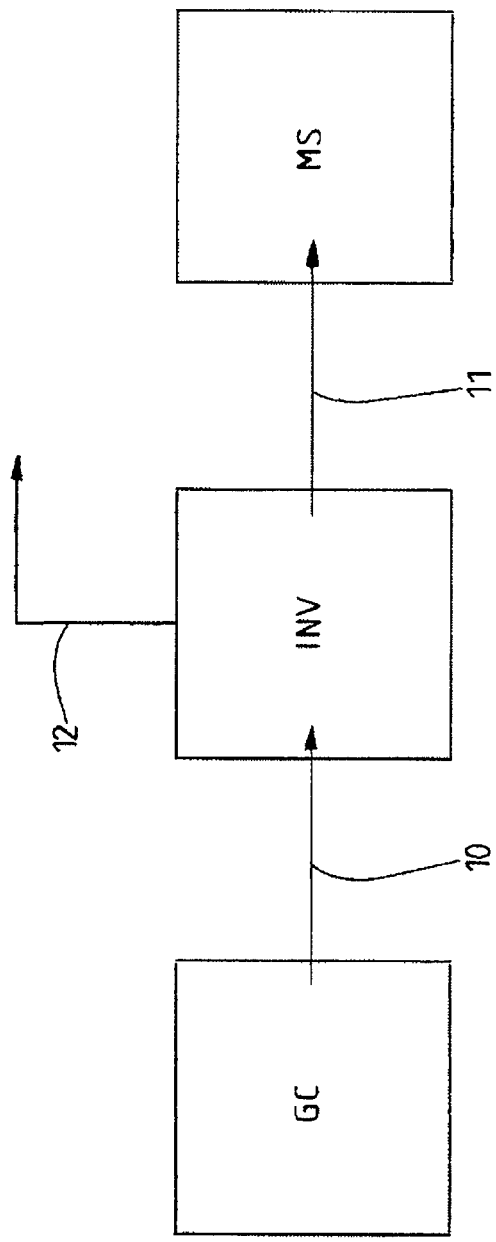
FIG. 1 shows an outline sketch for illustrating the arrangement of a device according to the invention in a system having a gas chromatograph and mass spectrometer.

According to FIG. 1, a device INV for preparing a gas stream is provided between a gas chromatograph GC and a mass spectrometer MS. The structure of the gas chromatograph GC with carrier gas source, injection apparatus, separation column etc. is known and need not be described in more detail. The same applies to the mass spectrometer MS with inlet system, ion source, mass analyzer, vacuum system, detector and data processing. Said preparation device INV can be a part of the inlet system in the mass spectrometer. The latter is preferably provided for determining isotope ratios and is then designed an IRMS.

A gas stream which, as carrier gas, contains helium or another inert gas, and also one or more gaseous analytes, passes into the preparation device INV from the GC or from another apparatus. These analytes are simple gases as pure as possible which are preferably suitable for an isotope analysis, such as $CO_2$ and $N_2$.

The gas stream 10 coming from the GC generally contains more carrier gas than the mass spectrometer can usefully receive. An excess of helium molecules especially leads to a reduction of sensitivity and possibly also to a falsification of the measurement results. A reduction of the gas stream 10 is therefore necessary. To date, however, the mass stream of the analyte molecules is also decreased thereby. The purpose is therefore separating off carrier gas molecules from the gas stream while retaining the analyte molecules. If, however, analyte molecules are separated off in conjunction, fractionation of the analyte molecules, in particular isotope fractionation should be avoided. To achieve this object, the preparation device INV is constructed in a particular manner. A residual gas stream 11 exiting from the preparation device INV in the direction towards the mass spectrometer is enriched with analyte molecules by separating off some of the carrier gas. A separated carrier gas stream 12 contains only carrier gas or a lower proportion of analyte molecules than the gas stream 10.

Figure 2:
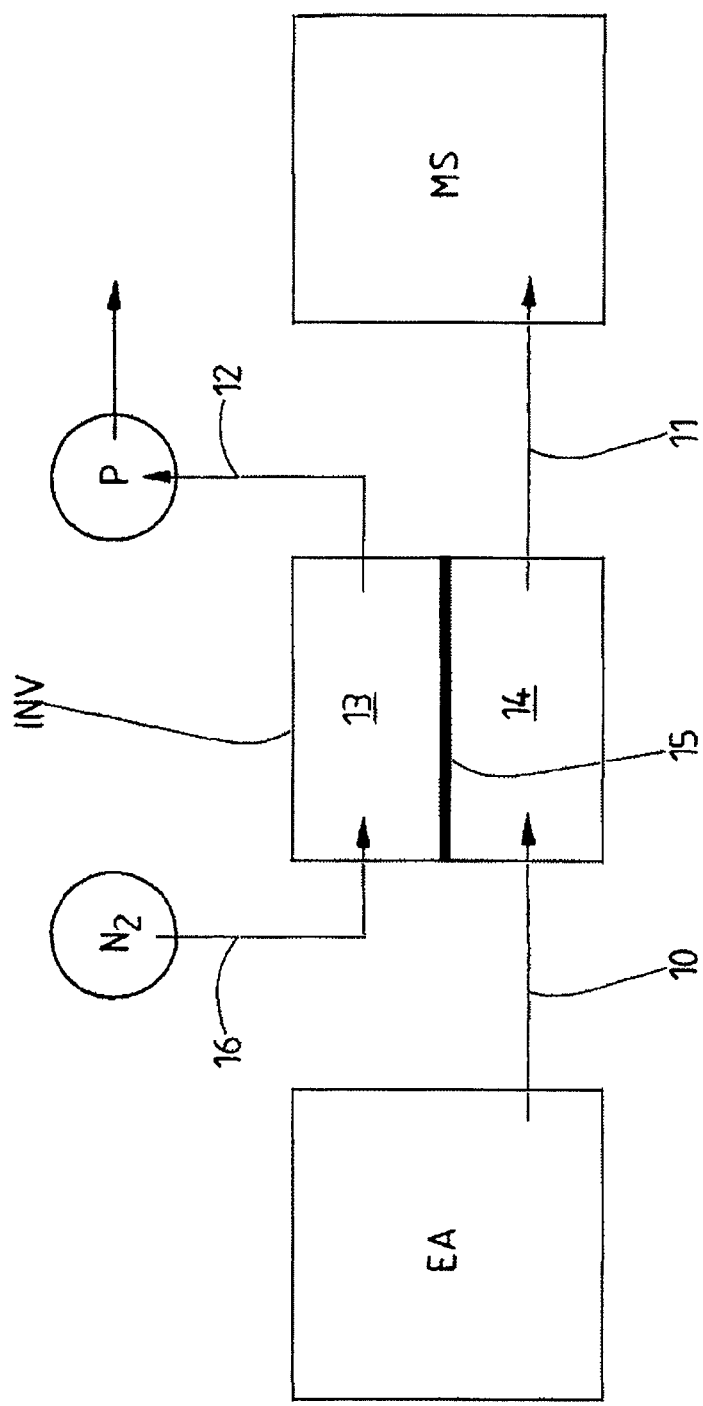
FIG. 2 shows an outline sketch of the device according to the invention between element analyzer and mass spectrometer.

The preparation device INV can be constructed in varying ways. A physically acting selective separating appliance, the outline structure of which is shown in FIG. 2, is advantageous. In the preparation device INV, two volumes 13, 14 are separated from one another by a wall 15 of a membrane type. The wall 15 is constructed in such a manner that carrier gas molecules can diffuse from the volume 14 conducting the gas stream 10 to the volume 13 conducting the separated carrier gas stream 12. The process can be supported by a reduced pressure in the volume 13 relative to the volume 14, generated by a pump P in the carrier gas stream 12. The composition of the residual gas stream 11 is dependent on the size and permeability of the wall 15, on the reduced pressure of the volume 13 and on the mass flow rate of the gas stream 10 and also possibly on other variables. In FIG. 2, instead of the GC, an element analyzer EA is provided. The latter is a high-temperature furnace which decomposes complex compounds into simpler gases.

Alternatively, or in addition to generating the reduced pressure in the volume 13, purging of the volume 13 can be provided. A purging gas stream 16, for example from a nitrogen reservoir $N_2$, expels the carrier gas from the volume 13. In this case, the permeation of the helium through the membrane is driven by the difference between the partial pressures. Virtually independently of the total pressure, the helium is driven from the zone of higher helium partial pressure to the zone of lower partial pressure.

Figure 3:
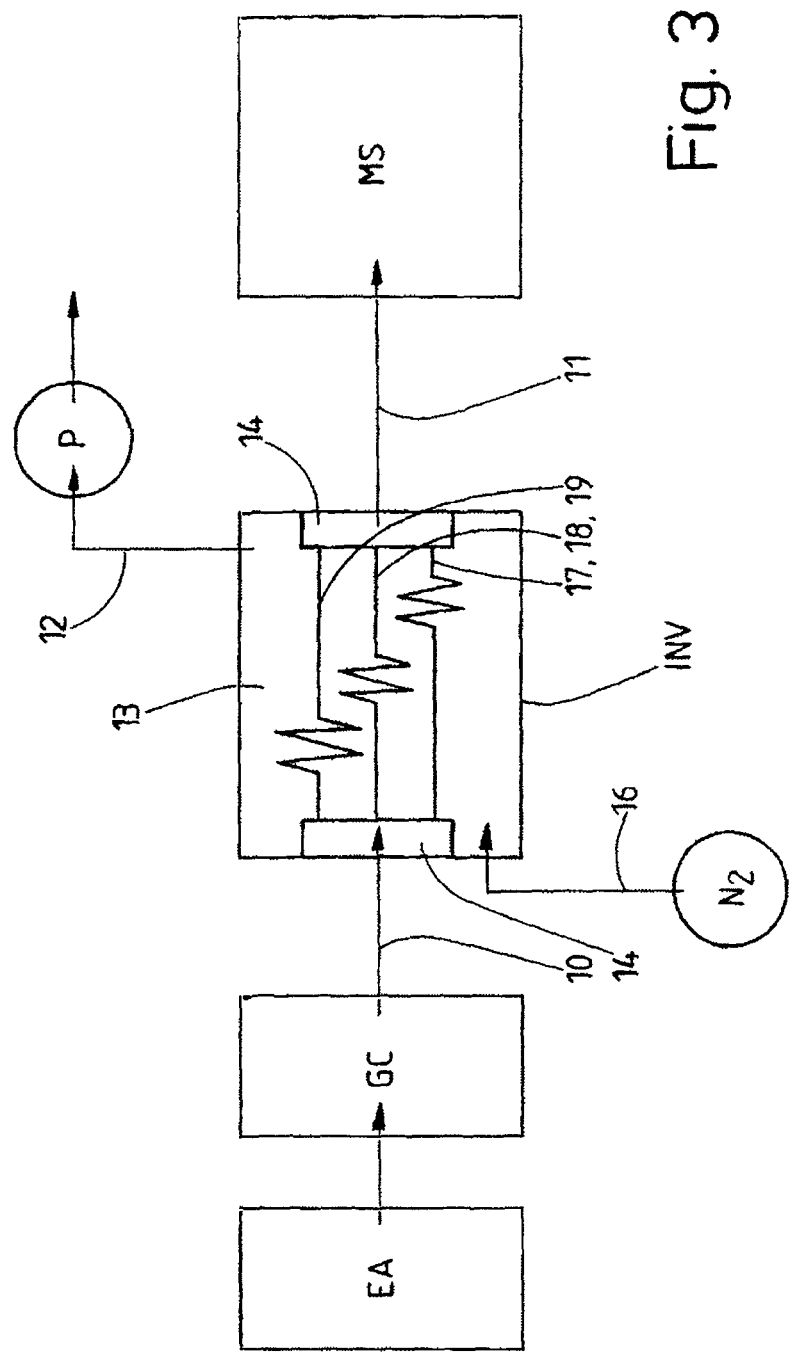
FIG. 3 shows a sketch analogous to FIG. 2, but with a modified device according to the invention for preparing the gas stream before feed of same into the mass spectrometer.

FIG. 3 shows the preparation device INV having a drastically increased surface area of the wall separating the volumes 13 and 14. This wall is formed here by the walls of a plurality of capillaries, 17, 18, 19 that are permeable to the carrier gas. The inner volume of the capillaries is functionally assigned to the volume 14, whereas the capillaries are surrounded by the volume 13. The capillaries 17 to 19 are each more or least tightly coiled to form packages and act as selective separating appliances for separating off some of the carrier gas from the gas stream.

Here, a combination of EA and GC is arranged upstream of the preparation device INV. Depending on the application, alternatively only an EA or GC can be provided.

The preparation device INV can be provided with a heating appliance. Alternatively, or in addition, a heated purging gas stream 16 can be supplied.

The selectively acting separating appliance or the wall 15 or the capillaries 17 to 19 can be produced from the most varied materials. The permeability to the carrier gas in combination with a sought-after non-permeability to the analyte molecules is of importance. Materials which come into consideration are, for example, quartz ($SiO_2$) and various plastics.

Figure 4:
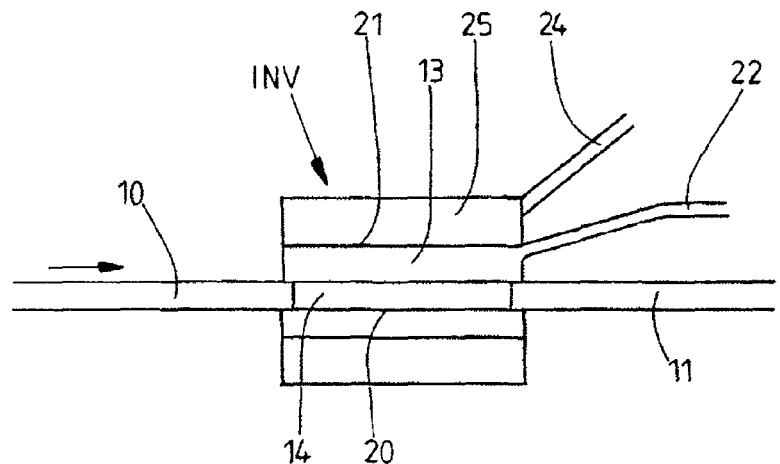
FIG. 4 shows a modified, namely multistage, device according to the invention.

The preparation device INV, in the embodiment according to FIG. 4, is configured in a particular manner. In the interior of the device, between the gas stream 10 and the residual gas stream 11, a capillary 20 is placed which has a permeable wall in the manner of a membrane, corresponding to the wall 15 and corresponding to the capillaries 17 to 19. The capillary 20 is surrounded by a chamber 21 here of the type of a tube and for forming the volume 13 around the capillary 20. A line 22 is attached to the chamber 21.

An outer chamber 23 is formed around the chamber 21. An outer wall of the chamber 21 is corresponding to the capillary 20 constructed in the manner of a membrane. A discharge line 24 is attached to the outer chamber 23.

Via the wall of the capillary 20, carrier gas from the gas stream 10 is discharged into the chamber 21. The amount of carrier gas then present in the volume 13 can be discharged via the line 22 or fed to the mass spectrometer MS. The latter makes it possible to monitor the quality of the membrane function of the capillary 20. If analyte gasses are also discharged via the capillary 20, these are detectable in the mass spectrometer. Similarly thereto, the carrier gas stream 12 in the FIGS. 1 to 3 can also be fed to the mass spectrometer for examination.

The membrane-like wall of the chamber 21 acts as a second separation stage for the carrier gas, subsequently to the capillary 20 as a first separation stage. It is possible thereby to separate any analyte molecules still present in the volume 13 substantially from the carrier gas and recirculate them via the line 22 to the residual gas stream 11. The outer chamber 23 defines a volume 25 for the separated carrier gas which then passes into the discharge line 24.

It is also possible to compare the isotope ratios in the two analyte-containing gas streams—residual gas stream 11 on the one hand and in the line 22 on the other. In the case of deviations, the isotope ratio determined in the residual gas stream 11 can be corrected on the basis of the result for the gas stream in the line 22.

Figure 5:
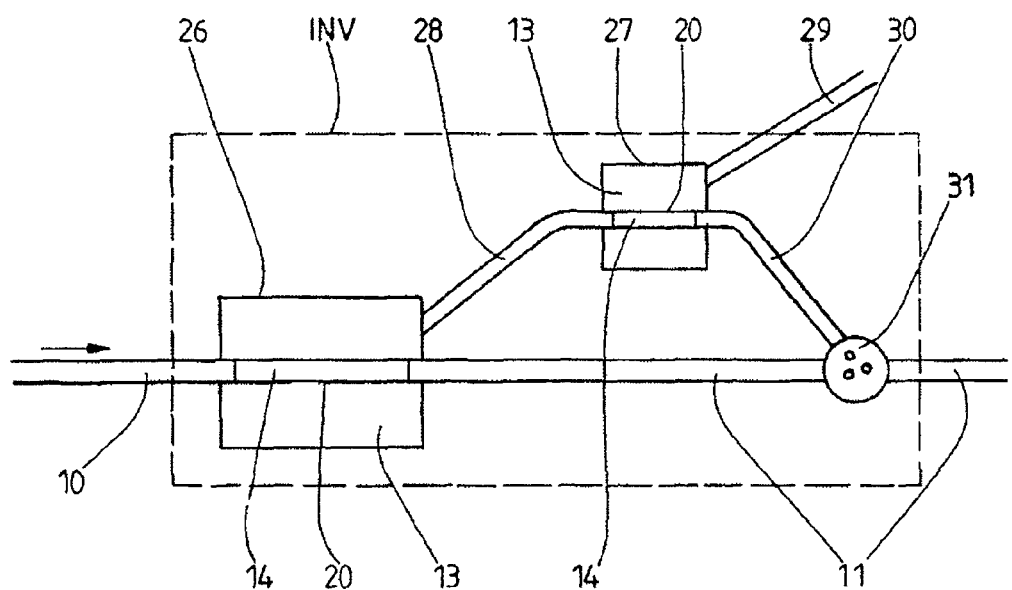
FIG. 5 shows a further alternative of a multistage device similar to FIG. 4.

A modification to FIG. 4 is shown in FIG. 5. The device INV is here likewise constructed in a multistage manner having a first stage 26 and a second stage 27. Via the permeable capillary 20, carrier gas passes into the outer volume 13 of the first stage 26 and from there via a line 28 into the second stage 27 which can be constructed in exactly the same manner as the first stage 26. Any analyte molecules still present in the carrier gas stream of the line 28 can be retained in the second stage 27 via the membrane-like wall of the capillary 20, while the carrier gas passes into the volume 13 of the second stage 27 and can be disposed of via a discharge line 29. To the capillary 20 of the second stage 27 is attached a line 30, the gas stream of which can be combined via a valve 31 with the residual gas stream 11, or instead of same, can be fed to the mass spectrometer.

A further embodiment of a device according to the invention is given by modifying the reactor shown in DE 10 2005 049 152 (there number 11). The channel plate provided there is covered on one side or both sides by a membrane. Between membrane and covers there are provided cavities for conducting away the helium that is separated off.

Various materials come into consideration as membranes for separating off helium from the gas stream 10 and are known in part from quite different fields of application. For example, membranes are provided in fuel cells, in electrolyte condensers, in lithium-ion accumulators. Corresponding membranes are used for separating off oxygen from reformed gas, for hydrogen recovery in petrochemical plants or in ammonia synthesis. The membranes used, owing to the size of the helium molecules, are preferably permeable to these. However, it is also possible to match the chemical properties of the membranes to the desired permeability to helium.

U.S. Pat. No. 7,290,439 describes examples of helium-permeable membranes for use in an apparatus for seeking helium leaks. Inter alia, hot silicon dioxide (300° C. to 900° C.) and tetrafluoroethylene (Teflon) are cited there.

WO 2007/012388 discloses metal-coated plastic membranes, e.g. made of Teflon and polyetherketones. Such membranes, even without a metal coating, are expected to be suitable for separating off helium.

Finally, polyimide-based gas-permeable membranes are known from accumulators. In addition, other plastics having what is termed an open crosslinking structure come into consideration as membranes.

LIST OF REFERENCE SIGNS 10 gas stream
11 residual gas stream
12 carrier gas stream
13 volume
14 volume
15 wall
16 purging gas stream
17 capillary
18 capillary
19 capillary
20 capillary
21 chamber
22 line
23 outer chamber
24 discharge line
25 volume
26 first stage
27 second stage
28 line
29 discharge line
30 line
31 valve
MS mass spectrometer
$N_2$ purging gas source
P pump
EA element analyzer
GC gas chromatograph
INV preparation device

The invention claimed is:

1. A device for preparing a gas stream for delivery to an operatively coupled isotope ratio mass analyzer, wherein the gas stream contains at least one analyte and a carrier gas comprising helium, the device including: a selectively acting separating appliance for separating off some of the carrier gas from the gas stream and for forming a residual gas stream and a separated carrier gas stream, wherein in the residual gas stream there is a higher proportion of the analyte than in the gas stream and wherein the selectively acting separating appliance has at least one capillary having a wall that is permeable to the carrier gas but that is substantially non-permeable to the at least one analyte, whereby the separating appliance does not change the isotope ratios of the at least one analyte in the gas stream.

2. The device as claimed in claim 1, wherein the at least one capillary is constructed from a material that is non-permeable to the at least one analyte, the material comprising at least one of silica ($SiO_2$) and a polymer.

3. The device as claimed in claim 1, including a volume conducting the separated carrier gas stream, which volume has a reduced pressure compared with a volume conducting the gas stream.

4. The device as claimed in claim 1 including a pump appliance for pumping off the separated carrier gas stream.

5. The device as claimed in claim 1 including a purging appliance for purging the volume conducting the separated carrier gas stream.

6. The device as claimed in claim 1, including a volume attached to the outside of the capillaries, which volume has a reduced pressure compared with the interior of the capillaries.

7. The device as claimed in claim 1 including a purging appliance for purging a volume attached to the outside of the capillaries.

8. A method for preparing a gas stream for delivery to an operatively coupled isotope ratio mass analyzer, wherein the gas stream comprises at least one analyte and a carrier gas comprising helium, the method including: separating a carrier gas stream from the gas stream forming a residual gas stream containing the at least one analyte wherein in the residual gas stream there is a higher proportion of the analyte than in the gas stream; and wherein the step of separating includes causing a portion of the carrier gas in the gas stream to pass through the walls of at least one capillary into a region exterior to the at least one capillary and wherein this step allows substantially none of the at least one analyte to pass through the walls of the at least one capillary.

9. The apparatus as claimed in claim 1 wherein the at least one capillary comprises a groove in a flat surface covered by a carrier gas permeable but analyte non-permeable membrane.

* * * * *